(12) United States Patent
Pamichev et al.

(10) Patent No.: US 11,359,620 B2
(45) Date of Patent: Jun. 14, 2022

(54) HEAT EXCHANGE SYSTEM FOR PATIENT TEMPERATURE CONTROL WITH EASY LOADING HIGH PERFORMANCE PERISTALTIC PUMP

(71) Applicant: Zoll Circulation, Inc., San Jose, CA (US)

(72) Inventors: Christo Petrov Pamichev, Cupertino, CA (US); Jeremy Thomas Dabrowiak, Santa Clara, CA (US)

(73) Assignee: ZOLL Circulation, Inc., San Jose, CA (US)

( * ) Notice: Subject to any disclaimer, the term of this patent is extended or adjusted under 35 U.S.C. 154(b) by 99 days.

(21) Appl. No.: 14/676,682

(22) Filed: Apr. 1, 2015

(65) Prior Publication Data
US 2016/0290330 A1 Oct. 6, 2016

(51) Int. Cl.
*F04B 43/12* (2006.01)

(52) U.S. Cl.
CPC ...... *F04B 43/1261* (2013.01); *F04B 43/1276* (2013.01)

(58) Field of Classification Search
CPC .. F04B 43/1261; F04B 43/1284; F04B 45/08; F04B 43/1276; A61M 1/1039; A61M 5/14232; A61F 7/12; A61F 2007/126
USPC .................................................. 417/477.11
See application file for complete search history.

(56) References Cited

U.S. PATENT DOCUMENTS

| | | | |
|---|---|---|---|
| 1,459,112 | A | 6/1923 | Mehl |
| 1,726,761 | A | 9/1929 | Palmer |
| 1,857,031 | A | 5/1932 | Schaffer |
| 2,663,030 | A | 12/1953 | Dahlberg |

(Continued)

FOREIGN PATENT DOCUMENTS

| | | |
|---|---|---|
| CN | 101090685 A | 12/2007 |
| DE | 19531935 | 2/1997 |

(Continued)

OTHER PUBLICATIONS

Wilhelm Behringer, Stephan Prueckner, Rainer Kenter, Samuel A. Tisherman, Ann Radovsky, Robert Clark S. William Stezoski, Heremy Henchir, Edwin Klein, Peter Safar, "Rapid Hypothermic Aortic Flush Can Achieve Survival without Brain Damage after 30 Minutes Cardiac Arrest in Dogs". anesthesiology. V. 93, No. 6, Dec. 2000.

(Continued)

*Primary Examiner* — Nathan C Zollinger
(74) *Attorney, Agent, or Firm* — Zoll Circulation, Inc.

(57) ABSTRACT

A peristaltic pump has an arcuate raceway wife a partially concave inner surface extending through an arc of at least one hundred eighty degrees (180°). The are defines a midpoint, and a rotor faces the inner surface of the raceway and is both rotatable relative to the raceway and transitionally movable relative to the raceway between a pump position, wherein the rotor is spaced from the midpoint a first distance, and a tube load position, wherein the rotor is spaced from the midpoint a second distance greater than the first distance. A rotor motor is coupled to the rotor to rotate the (Continued)

rotor and rollers arranged on the rotor to contact tubing disposed between the rotor and the raceway when the rotor is in the pump position. A loading motor moves the rotor toward and away from the raceway.

20 Claims, 8 Drawing Sheets (56) References Cited

U.S. PATENT DOCUMENTS

| | | | |
|---|---|---|---|
| 2,673,987 A | 4/1954 | Upshaw et al. | |
| 2,696,173 A * | 12/1954 | Jensen | F04B 43/0072 |
| | | | 417/477.6 |
| 2,893,324 A * | 7/1959 | Isreeli | F04B 43/1223 |
| | | | 417/477.14 |
| 2,987,004 A | 6/1961 | L | |
| 3,140,716 A | 7/1964 | Harrison et al. | |
| 3,225,191 A | 12/1965 | Calhoun | |
| 3,369,549 A | 2/1968 | Armao | |
| 3,425,419 A | 2/1969 | Dato | |
| 3,504,674 A | 4/1970 | Swenson et al. | |
| 3,725,259 A | 4/1973 | Webster, Jr. | |
| 3,744,555 A | 7/1973 | Fletcher et al. | |
| 3,751,077 A | 8/1973 | Hiszpanski | |
| 3,937,224 A | 2/1976 | Uecker | |
| 3,945,063 A | 3/1976 | Matsuura | |
| 4,038,519 A | 7/1977 | Foucras | |
| 4,065,264 A | 12/1977 | Lewin | |
| 4,103,511 A | 8/1978 | Kress et al. | |
| 4,126,132 A | 11/1978 | Portner et al. | |
| 4,153,048 A | 5/1979 | Magrini | |
| 4,173,228 A | 11/1979 | Van Steenwyk et al. | |
| 4,181,132 A | 1/1980 | Parks | |
| 4,181,245 A | 1/1980 | Garrett et al. | |
| 4,231,707 A * | 11/1980 | Tokorozawa | F04B 43/1253 |
| | | | 417/12 |
| 4,298,006 A | 11/1981 | Parks | |
| 4,459,468 A | 7/1984 | Bailey | |
| 4,532,414 A | 7/1985 | Shah et al. | |
| 4,552,516 A | 11/1985 | Stanley | |
| 4,554,793 A | 11/1985 | Harding, Jr. | |
| 4,558,996 A * | 12/1985 | Becker | F04B 43/1253 |
| | | | 417/374 |
| 4,581,017 A | 4/1986 | Sahota | |
| 4,638,436 A | 1/1987 | Badger et al. | |
| 4,653,987 A | 3/1987 | Tsuji et al. | |
| 4,661,094 A | 4/1987 | Simpson | |
| 4,665,391 A | 5/1987 | Spani | |
| 4,672,962 A | 6/1987 | Hershenson | |
| 4,754,752 A | 7/1988 | Ginsburg et al. | |
| 4,787,388 A | 11/1988 | Hofmann | |
| 4,813,855 A | 3/1989 | Leveen et al. | |
| 4,849,196 A | 7/1989 | Yamada et al. | |
| 4,852,567 A | 8/1989 | Sinofsky | |
| 4,860,744 A | 8/1989 | Johnson et al. | |
| 4,906,237 A | 3/1990 | Johansson et al. | |
| 4,925,376 A | 5/1990 | Kabler | |
| 4,941,475 A | 7/1990 | Williams et al. | |
| 4,976,590 A | 12/1990 | Baldwin | |
| 5,080,089 A | 1/1992 | Mason et al. | |
| 5,092,841 A | 3/1992 | Spears | |
| 5,096,393 A * | 3/1992 | Van Steenderen | F04B 43/1284 |
| | | | 604/153 |
| 5,103,360 A | 4/1992 | Maeda | |
| 5,106,360 A | 4/1992 | Ishiwara et al. | |
| 5,174,285 A | 12/1992 | Fontenot | |
| 5,192,274 A | 3/1993 | Bierman | |
| 5,195,965 A | 3/1993 | Shantha | |
| 5,211,631 A | 5/1993 | Sheaff | |
| 5,263,925 A | 11/1993 | Gilmore et al. | |
| 5,269,758 A | 12/1993 | Taheri | |
| 5,281,215 A | 1/1994 | Milder | |
| 5,304,214 A | 4/1994 | DeFord et al. | |
| 5,342,301 A | 8/1994 | Saab | |
| 5,344,436 A | 9/1994 | Fontenot et al. | |
| 5,370,675 A | 12/1994 | Edwards et al. | |
| 5,383,856 A | 1/1995 | Bersin | |
| 5,387,088 A * | 2/1995 | Knapp | F04B 43/1253 |
| | | | 417/477.1 |
| 5,403,281 A | 4/1995 | O'Neill et al. | |
| 5,433,588 A | 7/1995 | Monk et al. | |
| 5,433,740 A | 7/1995 | Yamaguchi | |
| 5,437,673 A | 8/1995 | Baust et al. | |
| 5,458,639 A | 10/1995 | Tsukashima et al. | |
| 5,466,208 A | 11/1995 | Jackson et al. | |
| 5,486,207 A | 1/1996 | Mahawili | |
| 5,507,792 A | 4/1996 | Mason et al. | |
| 5,531,714 A | 7/1996 | Dahn et al. | |
| 5,531,776 A | 7/1996 | Ward et al. | |
| 5,549,458 A * | 8/1996 | Chapman | F04B 43/1253 |
| | | | 417/360 |
| 5,624,392 A | 4/1997 | Saab | |
| 5,634,907 A | 6/1997 | Rani et al. | |
| 5,657,000 A * | 8/1997 | Ellingboe | F04B 43/1276 |
| | | | 340/608 |
| 5,676,670 A | 10/1997 | Kim | |
| 5,701,905 A | 12/1997 | Esch | |
| 5,706,889 A | 1/1998 | Bach et al. | |
| 5,709,564 A | 1/1998 | Yamada et al. | |
| 5,709,654 A | 1/1998 | Klatz et al. | |
| 5,711,654 A * | 1/1998 | Afflerbaugh | F04B 43/1253 |
| | | | 417/63 |
| 5,716,386 A | 2/1998 | Ward et al. | |
| 5,730,720 A | 3/1998 | Sites et al. | |
| 5,733,319 A | 3/1998 | Neilson et al. | |
| 5,737,782 A | 4/1998 | Matsuura et al. | |
| 5,746,585 A * | 5/1998 | McDunn | F04B 43/1261 |
| | | | 417/477.1 |
| 5,746,885 A | 5/1998 | McDunn | |
| 5,759,017 A | 6/1998 | Patton et al. | |
| 5,776,079 A | 7/1998 | Cope et al. | |
| 5,788,647 A | 8/1998 | Eggers | |
| 5,837,003 A | 11/1998 | Ginsburg | |
| 5,857,843 A * | 1/1999 | Leason | A61J 1/05 |
| | | | 417/360 |
| 5,862,675 A | 1/1999 | Scaringe et al. | |
| 5,879,329 A | 3/1999 | Ginsburg | |
| 5,895,418 A | 4/1999 | Saringer | |
| 5,906,407 A | 6/1999 | Frazee Et Ei | |
| 5,957,963 A | 9/1999 | Dobak, III | |
| 5,980,561 A | 11/1999 | Kolen et al. | |
| 5,989,238 A | 11/1999 | Ginsburg | |
| 6,019,783 A | 2/2000 | Philips et al. | |
| 6,042,559 A | 3/2000 | Dobak, III | |
| 6,051,019 A | 4/2000 | Dobak, III | |
| 6,059,825 A | 5/2000 | Hobbs et al. | |
| 6,096,068 A | 8/2000 | Dobak, III et al. | |
| 6,110,139 A | 8/2000 | Loubser | |
| 6,110,168 A | 8/2000 | Ginsburg | |
| 6,117,065 A | 9/2000 | Hastings et al. | |
| 6,117,105 A | 9/2000 | Bresnaham et al. | |
| 6,124,452 A | 9/2000 | Di Magno | |
| 6,126,684 A | 10/2000 | Gobin et al. | |
| 6,146,141 A | 11/2000 | Schumann | |
| 6,146,411 A | 11/2000 | Noda et al. | |
| 6,148,634 A | 11/2000 | Sherwood | |
| 6,149,670 A | 11/2000 | Worthen et al. | |
| 6,149,673 A | 11/2000 | Ginsburg | |
| 6,149,676 A | 11/2000 | Ginsburg | |
| 6,149,677 A | 11/2000 | Dobak, III | |
| 6,149,806 A | 11/2000 | Baer | |
| 6,165,207 A | 12/2000 | Balding | |
| 6,188,930 B1 | 2/2001 | Carson et al. | |
| 6,197,045 B1 | 3/2001 | Carson et al. | |
| 6,224,624 B1 | 5/2001 | Lasheras | |
| 6,231,594 B1 | 5/2001 | Dae | |
| 6,231,595 B1 | 5/2001 | Dobak | |
| 6,235,048 B1 | 5/2001 | Dobak | |
| 6,238,428 B1 | 5/2001 | Werneth | |
| 6,245,095 B1 | 6/2001 | Dobak | |
| 6,251,129 B1 | 6/2001 | Dobak | |
| 6,251,130 B1 | 6/2001 | Dobak | |
| 6,254,626 B1 | 7/2001 | Dobak | |

(56) References Cited

U.S. PATENT DOCUMENTS

| | | |
|---|---|---|
| 6,261,312 B1 | 7/2001 | Dobak |
| 6,264,679 B1 | 7/2001 | Keller |
| 6,283,940 B1 | 9/2001 | Mulholland |
| 6,287,326 B1 | 9/2001 | Pecor |
| 6,290,717 B1 | 9/2001 | Philips et al. |
| 6,299,599 B1 | 10/2001 | Pham et al. |
| 6,306,161 B1 | 10/2001 | Ginsburg |
| 6,312,452 B1 | 11/2001 | Dobak |
| 6,325,818 B1 | 12/2001 | Werneth |
| 6,338,727 B1 | 1/2002 | Noda et al. |
| 6,364,899 B1 | 4/2002 | Dobak |
| 6,368,304 B1 | 4/2002 | Aliberto |
| 6,375,674 B1 | 4/2002 | Carson et al. |
| 6,379,378 B1 | 4/2002 | Werneth |
| 6,383,144 B1 | 5/2002 | Mooney et al. |
| 6,383,210 B1 | 5/2002 | Magers |
| 6,387,326 B1 | 5/2002 | Edwards et al. |
| 6,393,320 B2 | 5/2002 | Lasersohn |
| 6,399,599 B1 | 6/2002 | Albert |
| 6,405,080 B1 | 6/2002 | Lasersohn |
| 6,409,747 B1 | 6/2002 | Gobin et al. |
| 6,416,533 B1 | 7/2002 | Gobin et al. |
| 6,428,563 B1 | 8/2002 | Keller |
| 6,440,468 B1 | 8/2002 | Quintanilla |
| 6,450,990 B1 | 9/2002 | Walker et al. |
| 6,461,379 B1 | 10/2002 | Carson et al. |
| 6,464,666 B1 | 10/2002 | Augustine et al. |
| 6,464,716 B1 | 10/2002 | Dobak, III et al. |
| 6,527,798 B2 | 3/2003 | Ginsburg et al. |
| 6,530,946 B1 | 3/2003 | Noda et al. |
| 6,544,282 B1 | 4/2003 | Dae et al. |
| 6,551,309 B1 | 4/2003 | Le Pivert |
| 6,554,791 B1 | 4/2003 | Cartledge et al. |
| 6,605,106 B2 | 8/2003 | Schwartz |
| 6,610,083 B2 | 8/2003 | Keller et al. |
| 6,620,187 B2 | 9/2003 | Carson et al. |
| 6,620,188 B1 | 9/2003 | Ginsburg et al. |
| 6,624,679 B2 | 9/2003 | Tomaiuolo et al. |
| 6,635,076 B1 | 10/2003 | Ginsburg |
| 6,635,079 B2 | 10/2003 | Ginsburg |
| 6,645,232 B2 | 11/2003 | Carson et al. |
| 6,648,905 B2 | 11/2003 | Hoglund |
| 6,660,027 B2 | 12/2003 | Gruszecki |
| 6,669,715 B2 | 12/2003 | Hoglund |
| 6,673,098 B1 | 1/2004 | Machold et al. |
| 6,679,906 B2 | 1/2004 | Hammack et al. |
| 6,685,731 B2 | 2/2004 | Kushnir et al. |
| 6,685,733 B1 | 2/2004 | Dae et al. |
| 6,692,518 B2 | 2/2004 | Carson et al. |
| 6,695,874 B2 | 2/2004 | Machold et al. |
| 6,706,060 B2 | 3/2004 | Tzeng et al. |
| 6,716,188 B2 | 4/2004 | Noda et al. |
| 6,718,012 B2 | 4/2004 | Ein-Gal |
| 6,719,723 B2 | 4/2004 | Werneth |
| 6,719,779 B2 | 4/2004 | Daoud |
| 6,726,653 B2 | 4/2004 | Noda et al. |
| 6,740,109 B2 | 5/2004 | Dobak, III |
| 6,743,201 B1 | 6/2004 | Dönig et al. |
| 6,764,391 B1 | 7/2004 | Grant |
| 6,799,063 B2 | 9/2004 | Carson et al. |
| 6,799,342 B1 | 10/2004 | Jarmon |
| 6,802,855 B2 | 10/2004 | Ellingboe |
| 6,818,012 B2 | 11/2004 | Ellingboe |
| 6,827,728 B2 | 12/2004 | Ellingboe |
| 6,843,800 B1 | 1/2005 | Dobak, III |
| 6,878,156 B1 | 4/2005 | Noda |
| 6,887,263 B2 | 5/2005 | Bleam et al. |
| 6,893,419 B2 | 5/2005 | Noda et al. |
| 6,969,399 B2 | 11/2005 | Schock et al. |
| 7,070,612 B1 | 7/2006 | Collins et al. |
| 7,104,769 B2 | 9/2006 | Davis |
| 7,140,850 B2 | 11/2006 | Otis |
| 7,211,106 B2 | 5/2007 | Dobak |
| 7,510,569 B2 | 3/2009 | Dae et al. |
| 7,666,215 B2 | 2/2010 | Callister et al. |
| 7,713,036 B2 | 5/2010 | Kojima et al. |
| 7,822,485 B2 | 10/2010 | Collins |
| 7,848,193 B2 | 12/2010 | Dae et al. |
| 7,857,781 B2 | 12/2010 | Noda et al. |
| 7,892,269 B2 | 2/2011 | Collins et al. |
| 7,914,564 B2 | 3/2011 | Magers |
| 8,105,262 B2 | 1/2012 | Noda et al. |
| 8,105,263 B2 | 1/2012 | Noda et al. |
| 8,105,264 B2 | 1/2012 | Noda et al. |
| 8,109,894 B2 | 2/2012 | Noda et al. |
| 8,128,384 B2 | 3/2012 | Mou |
| 8,226,605 B2 | 7/2012 | Faries et al. |
| 8,272,857 B2 | 9/2012 | Norman et al. |
| 8,888,729 B2 | 11/2014 | Noda |
| 9,784,263 B2* | 10/2017 | Hendricks ........... F04B 43/1276 |
| 2001/0031433 A1 | 10/2001 | Walker et al. |
| 2001/0047196 A1 | 11/2001 | Ginsburg et al. |
| 2002/0013569 A1 | 1/2002 | Sterman et al. |
| 2002/0022823 A1 | 2/2002 | Luo et al. |
| 2002/0145525 A1 | 10/2002 | Friedman et al. |
| 2002/0183692 A1 | 12/2002 | Callister |
| 2002/0198579 A1 | 12/2002 | Khanna |
| 2003/0036496 A1 | 2/2003 | Elsner et al. |
| 2004/0026068 A1 | 2/2004 | Schmidt et al. |
| 2004/0089058 A1 | 5/2004 | De Haan et al. |
| 2004/0102825 A1 | 5/2004 | Daoud |
| 2004/0104018 A1 | 6/2004 | Hughes et al. |
| 2004/0143311 A1 | 7/2004 | Machold et al. |
| 2004/0210231 A1 | 10/2004 | Boucher et al. |
| 2005/0047925 A1* | 3/2005 | Davis .................. B41J 2/17596 |
| | | 417/53 |
| 2005/0053502 A1 | 3/2005 | Souza |
| 2005/0069437 A1* | 3/2005 | Mittelstein .......... F04B 43/1253 |
| | | 417/477.2 |
| 2005/0156744 A1 | 7/2005 | Pires |
| 2006/0064146 A1 | 3/2006 | Collins |
| 2006/0069418 A1 | 3/2006 | Schock et al. |
| 2006/0122673 A1 | 6/2006 | Callister et al. |
| 2006/0210424 A1 | 9/2006 | Mallett et al. |
| 2006/0293734 A1 | 12/2006 | Scott et al. |
| 2007/0007640 A1 | 1/2007 | Harnden et al. |
| 2007/0076401 A1 | 4/2007 | Carrez et al. |
| 2007/0156006 A1* | 7/2007 | Smith .................. A61M 1/1031 |
| | | 600/16 |
| 2008/0230530 A1 | 9/2008 | Augustine et al. |
| 2008/0262409 A1 | 10/2008 | Derrico et al. |
| 2008/0267599 A1 | 10/2008 | Arnold et al. |
| 2009/0160297 A1* | 6/2009 | Anikhindi ............. F25D 25/025 |
| | | 312/319.7 |
| 2009/0206778 A1* | 8/2009 | Roh ........................ F04B 35/04 |
| | | 318/127 |
| 2009/0247963 A1 | 10/2009 | Bleam et al. |
| 2009/0299287 A1 | 12/2009 | Carson et al. |
| 2010/0036486 A1* | 2/2010 | Mazur ................. A61M 1/1037 |
| | | 623/3.13 |
| 2010/0129248 A1 | 5/2010 | Mou |
| 2011/0022136 A1 | 1/2011 | Scott et al. |
| 2011/0046551 A1 | 2/2011 | Augustine et al. |
| 2011/0137249 A1 | 6/2011 | Collins et al. |
| 2011/0184253 A1 | 7/2011 | Archer et al. |
| 2011/0208278 A1 | 8/2011 | Machold et al. |
| 2011/0213305 A1 | 9/2011 | Jonsson et al. |
| 2012/0100023 A1* | 4/2012 | Hanazuka ........... A61M 5/14232 |
| | | 417/477.7 |
| 2012/0148415 A1* | 6/2012 | Brueckner .......... A61M 5/14232 |
| | | 417/1 |
| 2012/0158103 A1 | 6/2012 | Bledsoe |
| 2013/0071270 A1* | 3/2013 | Zupp .................. A61M 5/14232 |
| | | 417/477.1 |
| 2013/0079853 A1 | 3/2013 | Pasche |
| 2013/0178923 A1 | 7/2013 | Dabrowiak |
| 2013/0079855 A1 | 8/2013 | Helkowski |
| 2013/0331774 A1 | 12/2013 | Farrell et al. |
| 2014/0081202 A1 | 3/2014 | Tsoukalis |
| 2014/0094880 A1 | 4/2014 | Lim |
| 2014/0094882 A1 | 4/2014 | Lim |

(56) References Cited

U.S. PATENT DOCUMENTS

| | | | |
|---|---|---|---|
| 2014/0094883 | A1 | 4/2014 | Lim |
| 2016/0131127 | A1 | 5/2016 | Hendricks |
| 2018/0128258 | A1 | 5/2018 | Hendricks |

FOREIGN PATENT DOCUMENTS

| | | | | |
|---|---|---|---|---|
| DE | 102009050053 | A1 * | 5/2011 | .......... F04B 43/1276 |
| DE | 102009050053 | A1 | 5/2011 | |
| EP | 0663529 | A1 | 7/1995 | |
| EP | 0663529 | B1 | 5/1997 | |
| GB | 2040169 | | 8/1980 | |
| GB | 1183185 | | 2/1985 | |
| GB | 2212262 | | 7/1989 | |
| GB | 2383828 | | 7/2003 | |
| JP | S61100243 | A | 5/1986 | |
| JP | 09-215754 | | 8/1997 | |
| JP | 10-0527777 | | 5/1998 | |
| JP | 10-305103 | | 11/1998 | |
| JP | 2003524507 | A | 8/2003 | |
| JP | 2008531114 | A | 8/2008 | |
| JP | 2008539034 | A | 11/2008 | |
| WO | 1999901682 | | 2/1990 | |
| WO | 1993004727 | | 3/1993 | |
| WO | 1994000177 | | 1/1994 | |
| WO | 1994001177 | | 1/1994 | |
| WO | 95-03680 | | 2/1995 | |
| WO | 1997025011 | | 7/1997 | |
| WO | 1998024491 | | 6/1998 | |
| WO | 1998040017 | | 9/1998 | |
| WO | 2000010494 | | 3/2000 | |
| WO | 2001013809 | | 3/2001 | |
| WO | 0126719 | | 4/2001 | |
| WO | 2001064146 | | 9/2001 | |
| WO | 2001076517 | | 10/2001 | |
| WO | 2001083001 | | 11/2001 | |
| WO | 2014160422 | A1 | 10/2014 | |
| WO | 2015122938 | A1 | 8/2015 | |
| WO | 2012-0175089 | | 12/2021 | |

OTHER PUBLICATIONS

Dorraine Day Watts, Arthur Trask, Karen Soeken, Philip Predue, Sheilah Dols, Christopher Kaufman; "Hypothermic Coagulopathy in trauma: Effect of Varying levels of Hypothermia on Enzyme Speed, Platelet Function, and Fibrinolytic Activity". The Journal of Trauma: Injury, Infection, and Critical Care, Vo. 44, No. 5 (1998).

Jeremy Thomas Dabrowiak, "Heat Exchange System for Patient Temperature Control with Multiple Coolant Chambers for Multiple Heat Exchange Modalities", related pending U.S. Appl. No. 14/175,545 non-final office action dated Feb. 12, 2016.

Jeremy Thomas Dabrowiak, "Heat Exchange System for Patient Temperature Control with Multiple Coolant Chambers for Multiple Heat Exchange Modalities", related pending U.S. Appl. No. 14/175,545 applicants response to non-final office action filed May 2, 2016.

Jeremy Thomas Dabrowiak, Christoph Matthias Pistor, Craig Wendell Pendry, Christo Petrov Pamichev, "Fluid Cassette with Tensioned Polymeric Membranes for Patient Heat Exchange System" related pending U.S. Appl. No. 14/180,613, non-final office action dated May 19, 2016.

Christoph Matthias Pistor, Jeremy Thomas Dabrowiak, Craig Wendell Pendry, Christo Petrov Pamichev, "Fluid Cassette with Polymeric Membranes and Integral Intel and Outlet Tubes for Patient Heat Exchange System", related pending U.S. Appl. No. 14/180,655, non-final office action dated May 18, 2016.

Jeremy Thomas Dabrowiak, Eric Peterson, "Patient Heat Exchange System with Transparent Wall for Viewing Circulating Refrigerant", related pending U.S. Appl. No. 14/276,202, non-final office action dated May 19, 2016.

Jeremy Thomas Dabrowiak, Christoph Matthias Pistor, Craig Wendell Pendry, Christo Pamichev, "Fluid Cassette with Tensioned Polymeric Membranes for Patient Heat Exchange System", related pending U.S. Appl. No. 14/180,613, applicant's response to non-final office action filed Jun. 1, 2016.

Christoph Matthias Pistor, Jeremy Thomas Dabrowiak, Craig Wendell Pendry, Christo Pamichev, "Fluid Cassette with Polymeric Membranes and Integral Inlet and Outlet Tubes for Patient Heat Exchange System", related pending U.S. Appl. No. 14/180,655, applicant's response to non-final office action file Jun. 1, 2016.

Jeremy Thomas Dabrowiak, Eric Peterson, "Patient Heat Exchange System with Transparent Wall for Viewing Circulating Refrigerant", related pending U.S. Appl. No. 14/276,202, applicant's response to non-final office action filed Jun. 1, 2016.

Jeremy Thomas Dabrowiak, Craig Wendell Pendry, Christoph Matthias Pistor, "Patient Heat Exchange System with Two and Only Two Fluid Loops", related U.S. Appl. No. 14/180,719, Non-Final Office Action dated Jun. 7, 2016.

Jeremy Thomas Dabrowiak, Christoph Matthias Pistor, Craig Wendell Pendry, Christo Pamichev, "Fluid Cassette with Tensioned Polymeric Membranes for Patient Heat Exchange System", related pending U.S. Appl. No. 14/180,613 final office action dated Jul. 15, 2016.

Jeremy Thomas Dabrowiak, Eric Peterson, "Patient Heat Exchange System with Transparent Wall for Viewing Circulating Refrigerant", related pending U.S. Appl. No. 14/276,202 final office action dated Jul. 15, 2016.

Austin Reid Hendricks, Christo Petrov Pamichev, Venkata Vishnu Gurukula, Jeremy Thomas Dabrowiak, "Heat Exchange System for Patient Temperature Control with Easy Loading High Performance Peristaltic Pump", related U.S. Appl. No. 14/534,718, Non-Final Office Action dated Jul. 25, 2016.

Jeremy Thomas Dabrowiak, Craig Wendell Pendry, Christoph Matthias Pistor, "Patient Heat Exchange System with Two and Only Two Fluid Loops", related U.S. Appl. No. 14/180,719, Applicant's response to the Non-Final Office Action filed Sep. 7, 2016.

Christoph Matthias Pistor, Jeremy Thomas Dabrowiak, Craig Wendell Pendry, Christo Pamichev, "Fluid Cassette With Polymeric Membranes and Integral Inlet and Outlet Tubes for Patient Heat Exchange System", related U.S. Appl. No. 14/180,655, Final Office dated Sep. 8, 2016.

Christoph Matthias Pistor, Jeremy Thomas Dasrowiak, Craig Wendell Pendry, Christo Pamichev, "Fluid Cassette with Polymeric Membranes and Integral Intel and Outlet Tubes for Patient Heat Exchange System", file history of related U.S. Appl. No. 14/180,655, filed Feb. 14, 2014.

Jeremy Thomas Dasrowiak, Craig Wendell Pendry, Christoph Matthias Pistor, "Patient Heat Exchange System With Two and Only Two Fluid Loops", file history of related U.S. Appl. No. 14/180,719, filed Feb. 14, 2014.

Jeremy Thomas Dabrowiak, "Heat Exchange System for Patient Temperature Control with Multiple Coolant Chambers for Multiple Heat Exchange Modalities". file history of related U.S. Appl. No. 14/175,545, filed Feb. 7, 2014.

Jeremy Thomas Dabrowiak, Eric Peterson, "Patient Heat Exchange System with Transparent Wall for Viewing Circulating Refrigerant" file history of related application U.S. Appl. No. 14/276,202, filed May 13, 2014.

Austin Reid Hendricks, Christo Petrov Pamichev, Venkata Vishnu Gurukula, Jeremy Thomas Dabrowiak, "Heat Exchange System for Patient Temperature Control with Easy Loading High Performance Peristaltic Pump" file history of related U.S. Appl. No. 14/534,718, filed Nov. 6, 2014.

Jeremy Thomas Dabrowiak, Christoph Matthias Pistor, Craig Wendell Pendry, Christo Pamichev, "Fluid Cassette with Tensioned Polymeric Membranes for Patient Heat Exchange System", file history of related U.S. Appl. No. 14/180,613, filed Feb. 14, 2014.

Jeremy Thomas Dabrowiak, Mark Davey, "Serpentine Heat Exchange Assembly for Removable Engagement with Patient Heat Exchange System", file history of related U.S. Appl. No. 14/675,421, filed Mar. 31, 2015.

Jeremy Thomas Dabrowiak, Craig Wendell Pendry, Christoph Matthias Pistor, "Cold Plate Design in Heat Exchanger for Intravascular Temperature Management Catheter and/or Heat Exchange Pad", file history of related U.S. Appl. No. 14/676,504, filed Mar. 31, 2016.

James Mazzone, "Proximal Mounting of Temperature Sensor in Intravascular Temperature Management Catheter", file history of related U.S. Appl. No. 14/675,452, filed Mar. 31, 2015.

Christo Petrov Pamichev, Jeremy Thomas Dabrowiak, "Working Fluid Cassette with Hinged Plenum or Enclosure for Interfacing (56) References Cited

OTHER PUBLICATIONS

Heat Exchanger with Intravascular Temperature Management Catheter", file history of related U.S. Appl. No. 14/676,672, filed Apr. 1, 2015.

Austin Reid Hendricks, Christo Petrov Pamichev, Venkata Vishnu Gurukula, Jeremy Thomas Dabrowiak, "Heat Exchange System for Patient Temperature Control with Easy Loading High Performance Peristaltic Pump", file history of related U.S. Appl. No. 15/711,276, filed Sep. 21, 2017.

Austin Reid Hendricks, Christo Petrov Pamichev, Venkata Vishnu Gurukula, Jeremy Thomas Dabrowiak, "Heat Exchange System for Patient Temperature Control with Easy Loading High Performance Peristaltic Pump", related European application No. 15857869.0 extended Search Report dated May 8, 2018.

Austin Reid Hendricks, Christo Petrov Pamichev, Venkata Vishnu Gurukula, Jeremy Thomas Dabrowiak, "Heat Exchange System for Patient Temperature Control with Easy Loading High Performance Peristaltic Pump", related U.S. Appl. No. 15/711,276, Non-Final Office Action dated Aug. 9, 2018.

Austin Reid Hendricks, Christo Petrov Pamichev, Venkata Vishnu Gurukula, Jeremy Thomas Dabrowiak, "Heat Exchange System for Patient Temperature Control with Easy Loading High Performance Peristaltic Pump", related U.S. Appl. No. 15/711,276, Non-Final Office Action dated Feb. 15, 2019.

American Urethane Inc., "Polyurethane Properties", available Oct. 12, 2010, http://web.archive.org/web/20101012211957/http://americanurethane.com/polyurethane-properties.html.

\* cited by examiner

HEAT EXCHANGE SYSTEM FOR PATIENT TEMPERATURE CONTROL WITH EASY LOADING HIGH PERFORMANCE PERISTALTIC PUMP

TECHNICAL FIELD

The present application relates generally to heat exchange systems for patient temperature control with easy loading high performance peristaltic pumps.

BACKGROUND

Patient temperature control systems have been introduced to prevent fever in patients in the neuro ICU due to suffering from sub-arachnoid hemorrhage or other neurologic malady such as stroke. Also, such systems have been used to induce mild or moderate hypothermia to improve the outcomes of patients suffering from such maladies as stroke, cardiac arrest, myocardial infarction, traumatic brain, injury, and high intracranial pressure. Examples of intravascular heat exchange catheters are disclosed in U.S. Pat. Nos. 7,914,564, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,549,677, 6,096,068, 6,042,559, 8,888,729, and USPPs 2013/0178923, 2013/0079855, 2013/0079856, 2014/0094880, 2014/0094882, 2014/0094883, all of which are incorporated herein by reference.

External patient temperature control systems may be used. Such systems are disclosed in U.S. Pat. Nos. 6,827,728, 6,818,012, 6,802,855, 6,799,063, 6,764,391, 6,692,518, 6,669,715, 6,660,027, 6,648,905, 6,645,232, 6,620,187, 6,461,379, 6,375,674, 6,197,045, and 6,188,930 (collectively, "the external pad patents"), all of which are incorporated herein by reference.

In general, in all of the intravascular and external, patient temperature control solutions, the temperature of the working fluid flowing through the catheter or pad is regulated by a heat-exchange console based on feedback provided by the patient's actual body temperature, typically core body temperature as may be variously measured rectally, esophageally, tympanic ear temperature, blood temperature in, e.g., the vena cava, etc. The working fluid temperature is regulated by thermally coupling the working fluid to heating and/or cooling elements in the console. In many cases, the working fluid is forced in a closed fluid circuit path (including the console and the catheter or pad) by a peristaltic pump acting on tubing, e.g., pump tubing or IV tubing, in the fluid circuit path.

SUMMARY

The following patent applications are hereby incorporated by reference herein in their entirety, Ser. No. 14/534,718, filed Nov. 6, 2014, filed concurrently herewith.

As understood herein, peristaltic pumps typically include a rotor for revolving one or more rollers against a tube, e.g., a pump tube or, IV tube, or other type of tubing, to force fluid through the tube by peristalsis, and an arcuate raceway against which the tube is urged by the rollers. The ease by which the tube can be loaded between the rollers and raceway competes with the performance of the pump: an easier to load pump typically has lower performance, whereas a higher performance pump (with higher pumping pressure and fluid flow) usually entails more complex loading of the tube. This is because in easy to load pumps, the raceway is typically movable sway from the rollers to facilitate easily placing the tube between the rollers and raceway, but higher performance pumps require longer raceways (e.g., greater than 180 degrees of arc) that are generally not movable away from the pump, complicating the task of loading the tube (which for high performance applications is relatively thick and inflexible compared, to low performance tubes) between the rollers and raceway.

Accordingly, a pump may have an arcuate raceway having a concave inner surface and a rotor facing the inner surface of the raceway. The rotor is rotatable relative to the raceway, and is translationally mounted relative to the raceway between a pump or operating position, wherein, the rotor is spaced from the midpoint a first distance, and a tube load position, wherein the rotor is spaced from the midpoint a second distance greater than the first distance. A rotor motor is coupled, to the rotor to rotate the rotor. One or more rollers are arranged on the rotor to contact, tubing disposed between the rotor and fee raceway at least when the rotor is in the pump position. A loading motor may be coupled to the rotor to move the rotor translationally and/or rotationally between the pump position and the tube load position.

In examples, an operating element such as a button may be provided that is manipulate by a person or controller to energize the loading motor.

In another aspect, a method includes rotating a peristaltic pump rotor relative to a raceway to urge fluid through a tube disposed between the raceway and the rotor, and energizing a loading motor to move the rotor away from the raceway.

In another aspect, a pump assembly has a raceway, a rotor spaced from the raceway, and a rotor motor configured to rotate the rotor to urge fluid through a tube disposed between the raceway and the rotor. A loading motor is coupled to the rotor to move the rotor translationally and/or rotationally relative to the raceway.

The details of the various embodiments described herein, both as to their-structure and operation, can best be understood in reference to the accompanying drawings, in which like reference numerals refer to like parts, and in which:

DETAILED DESCRIPTION

Figure 1:
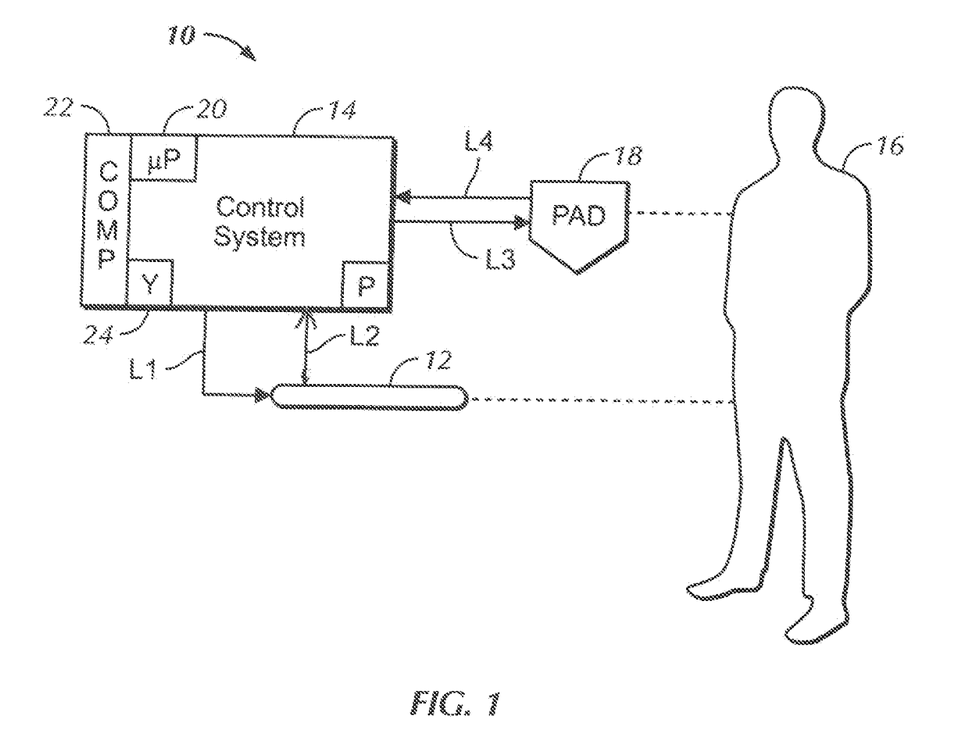
FIG. 1 is a schematic view of a non-limiting system in accordance with an embodiment.

Referring initially to FIG. 1, in accordance with present principles, a system 10 may include an intravascular heat exchange catheter 12 controlled by a control system 14 to control patient temperature, e.g., to prevent the patient 16 from becoming febrile or to induce therapeutic hypothermia in the patient 16. In the catheter, working fluid or coolant such as but not limited to saline circulates (typically under the influence of a pump "P" in the control system) in a closed loop from the control system 14, through, a fluid supply line L1, through the catheter 12, and back to the system 14 through a fluid return line L2, such that no working fluid or coolant enters the body. While certain preferred catheters are disclosed herein, it is to be understood that other catheters can be used in accordance with present principles, including, without limitation, any of the catheters disclosed above or in the following U.S. patents, all incorporated herein by reference: U.S. Pat. Nos. 5,486,208, 5,837,003, 6,110,168, 6,149,673, 6,149,676, 6,231,594, 6,264,679, 6,306,161, 6,235,048, 6,238,428, 6,245,095, 6,251,129, 6,251,130, 6,254,626, 6,261,312, 6,312,452, 6,325,818, 6,409,747, 6,368,304, 6,338,727, 6,299,599, 6,287,326, 6,126,684, 7,211,106. The catheter 12 may be placed in the venous system, e.g., in the superior or inferior vena cava.

Instead of or in addition to the catheter 12, the system 10 may include one or more pads 18 that are positioned against the external skin of the patient 16 (only one pad 18 shown for clarity). The pad 18 may be, without limitation, any one of the pads disclosed in the external pad patents. The temperature of the pad 18 can be controlled by the control system 14 to exchange heat with the patient 16, including to induce therapeutic mild or moderate hypothermia in the patient in response to the patient presenting with, e.g., cardiac arrest, myocardial infarction, stroke, high intracranial pressure, traumatic brain injury, or other malady die effects of which can be ameliorated by hypothermia. The pad 18 may receive working fluid from the system 14 through a fluid supply line L3, and return working fluid to the system 14 through a fluid return, line L4, The pump "P" may be a peristaltic pump which engages any one of the lines L1-L4, which are typically plastic IV lines, to urge working fluid through the lines through, peristalsis.

The control system 14 may include one or more microprocessors 20 receiving target and patient temperatures as input and controlling, among other things, the pump "P" and a refrigerant compressor 22 and/or a bypass valve 24 that can be opened to permit refrigerant to bypass a condenser.

Turning now to FIGS. 2-5, an example of the pump "P" in FIG. 1 is shown and generally designated 30. The pump 30 includes a rigid, preferably metal or hard plastic raceway 32 or channel and a rotor 34. The raceway 32 may be formed from one or more blocks of material as shown and has an inner arcuate surface 36 which may have a substantially constant radius of curvature. In some examples, the arcuate surface 36, which defines a midpoint 38 between its two ends 40, 42 (labeled in FIG. 3), can extend through an arc of at least one hundred eighty degrees (180°) (e.g., where two drive rollers are used) and may extend through an arc of between one hundred eighty degrees (180°) and two hundred seventy degrees (270°). In the example shown, the arcuate surface 36 extends, from one end 40 to the other end 42, through an are of greater than 200°. For example, the arc may be about 210° to 230°. In certain embodiments, the arcuate surface of a raceway may extend through an arc equal to 360° divided by n, where n is equal to the number of drive rollers mounted on or near a rotor which is rotated relative to the raceway.

Figure 2:
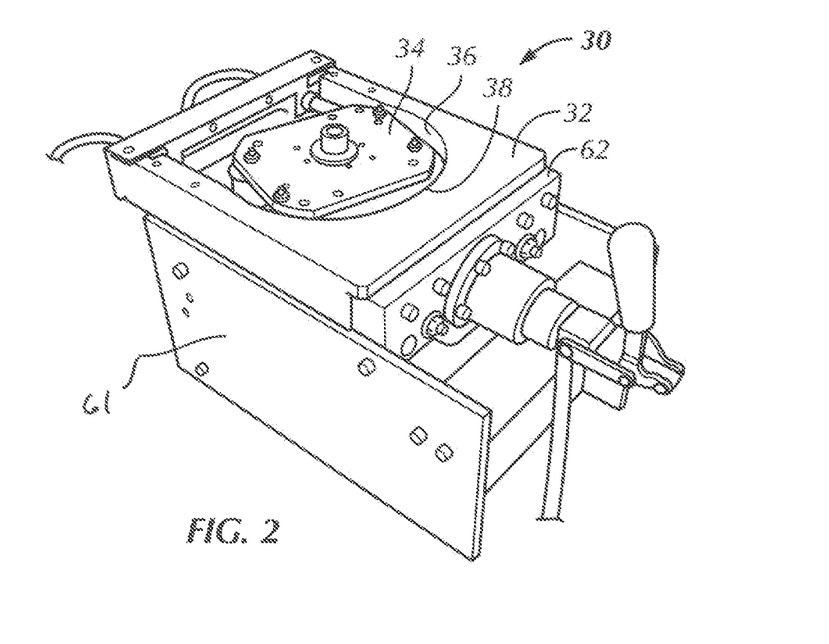
FIG. 2 is a perspective view of the pump with the rotor in the pump position.
Figure 3:
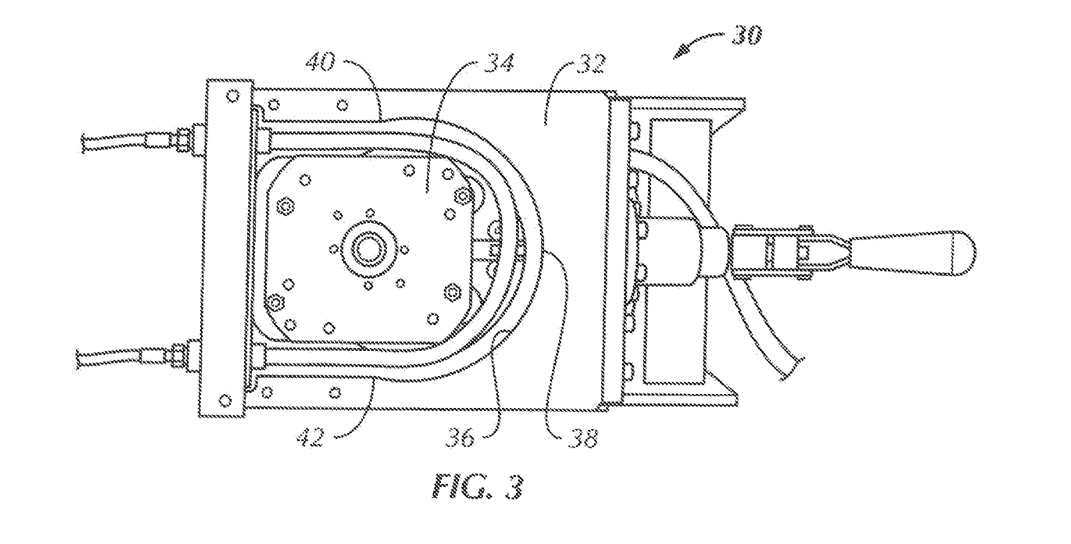
FIG. 3 is a top view of the pump with the rotor in the pump position.
Figure 4:
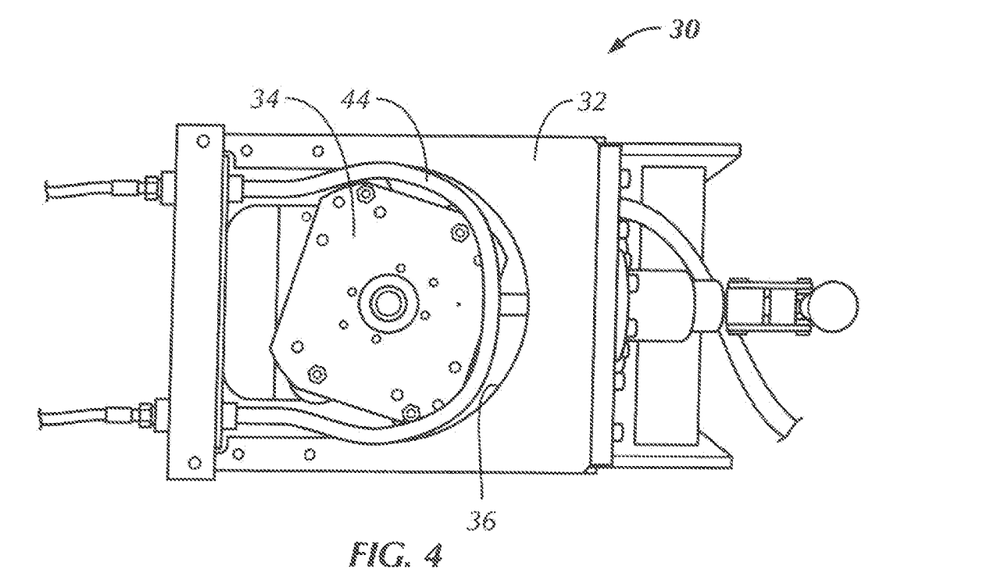
FIG. 4 is a perspective view of the pump with the rotor in the tube load position, illustrating a person manually loading the tube between the raceway and the rotor.
Figure 5:
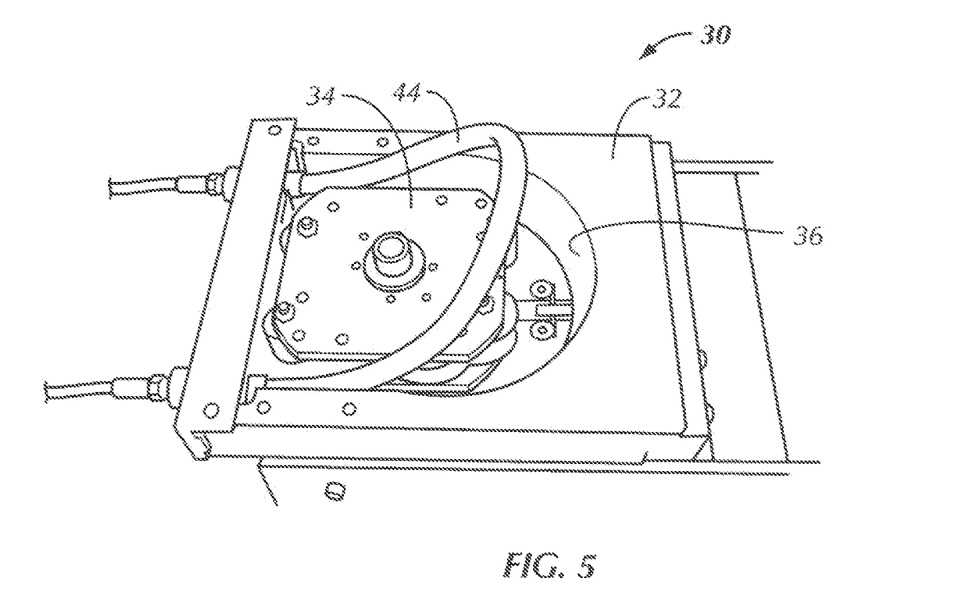
FIG. 5 is a top view of the pump with the rotor in the tube load position.

Covering more than 180° degrees of arc with the raceway may provide additional benefits, such as an extra margin against internal leakage. Furthermore, it is possible that covering more than 180° degrees of are allows the tubing to open gradually alter being compressed by a drive roller and thereby reduce the degree of pulsatility of the flow. This in turn can reduce the amount of unwanted movement experienced by the downstream tubing and catheter when subject to pulsating flow. A motor, described further below, rotates the rotor 34 relative to the raceway 32. As well, the rotor 34 is movable translationally and/or rotationally relative to the raceway 32 between a pump position (FIGS. 2, 3, 6, 7, and 9), in which fee rotor 34 is spaced from fee midpoint 38 of the inner surface 36 of the raceway 32 a first distance, and a tube load position (FIGS. 4, 5, and 8), in which the rotor 34 is spaced from the midpoint 38 a greater, second distance. As shown in FIGS. 2 and 3, in the pump position, rollers on the rotor 34 urge against a tube such as a pump tube or IV tube that is disposed between the rollers and the raceway 32. In the tube load position, the rotor 34 is sufficiently spaced from the raceway 32 to permit a tube 44 to be disposed between the raceway 32 and rotor 34 and to be removed therefrom, e.g., by hand. Example mechanisms for moving the rotor translationally and/or rotationally are discussed further below.

Indeed and now referring to FIGS. 6-9 for example structure, mounted on the rotor 34 are one or more rollers to urge against the tube 44 to pump fluid through the tube. In the example shown in FIG. 6, the rotor 34 is defined in part by a rectilinear, non-square body, and on or near each corner of the body a roller is mounted, e.g., rotatably mounted to the rotor body. In the example, at one set of opposed corners on the body, drive rollers 46 are respectively mounted (only one drive roller shown in the perspective of FIG. 6), whereas at the other set of opposed corners on the body, guide rollers 48 are respectively mounted. Thus, between the drive rollers 46 are guide rollers 48.

Figure 6:
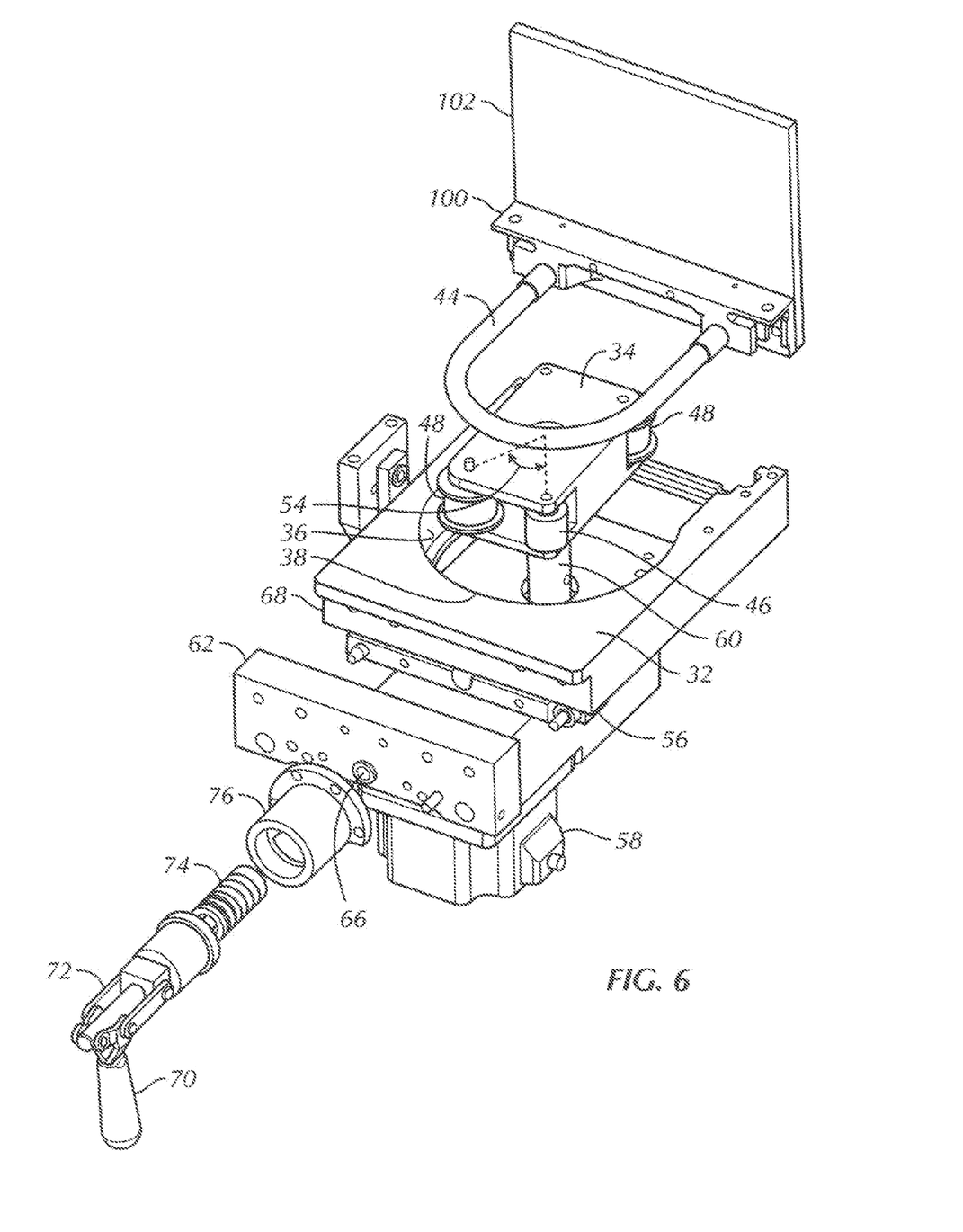
FIGS. 6 and 7 are exploded perspective views from the bottom and top, respectively, of the pump, illustrating features of an example embodiment, with portions broken away in FIG. 7.

As shown in FIG. 6, the drive roller 46 has a cylindrical or similar to cylindrical outer surface, and at least a portion of the outer surface is configured to urge against the tube 44. The outer surface of the example drive roller may be a single smooth cylinder and/or it may or may not have one or more flanges having peripheries extending beyond the cylindrical outer surface. In contrast, FIG. 7 best shows that the guide roller 48 also has a cylindrical (or similar) outer surface but in addition includes top and/or bottom flanges 50, 52 defining respective peripheries extending beyond the cylindrical outer surface of the guide roller such that the tube 44 can be received on the cylindrical outer surface of the guide roller between the flanges 50, 52 when the rotor is in the pump position, and is rotated. In the example shown, two and only two drive rollers 46 and two and only two guide rollers 48 are provided, but any number of drive and/or guide rollers may be utilized. In certain embodiments, the drive roller or guide roller may have a non-cylindrical or partially cylindrical outer surface.

Also, in the example shown, owing to the non-square shape of the rotor 34 body, the angle 54 between the drive roller 46 and guide roller 48 at one of the ends of the rotor body, with a vertex on a point on the roller body (e.g., the midpoint), is not ninety degrees. Instead, in the example shown, the angle 54 may be, for example, fifty five degrees. The same angle obtains at the opposite end of the rotor body.

However, in some embodiments the rotor body is square, in which case all rollers are separated from the adjacent rollers by ninety degrees.

A block-like motor mount 56 supports a motor 58 such as a small ac or dc motor, in some embodiments, a stepper motor or other appropriate motor type. The motor 58 is coupled to fee rotor 34 by an output shaft 60, with, in some embodiments, a reduction gear train (not shown) being meshed between the motor shaft and the output shaft 60.

A positioning mechanism is coupled to the motor mount 56 and is manipulable by a person to move the motor mount 56 to thereby move the rotor 34 between the pump position and the tube load position. In a non-limiting example, referring briefly back to FIG. 2, a base 61 stationary holds the raceway 32, and a rectilinear rigid support block 62 (FIGS. 2 and 6-9) may be bolted or welded to the base 61 or made integrally therewith. A push rod 64 (FIGS. 7-9) extends through a hole 66 in the support block 62 to contact and/or be engaged with the motor mount 56 and/or with a motor plate 68 coupled to the motor mount 56. A handle 70 is coupled at a hinge mechanism 72 to the push rod 64. The handle 70 can be moved by hand to a substantially perpendicular orientation relative to the push rod 64 (FIGS. 6 and 9) to pull the push rod 64 and thus to move the motor mount 56 (and hence rotor 34) toward the inner surface of the raceway 32, thereby moving the rotor 34 to the pump position. The handle 70 can also be moved by hand down from the perpendicular orientation to the non-perpendicular orientation shown in FIGS. 7 and 8. This pushes the push rod 64 and thus moves the motor mount 56/rotor 34 away from the pump position to the tube load position. One or more radial bearings 74, 76 may be provided as appropriate to radially support elements of the positioning mechanism.

Figure 7:
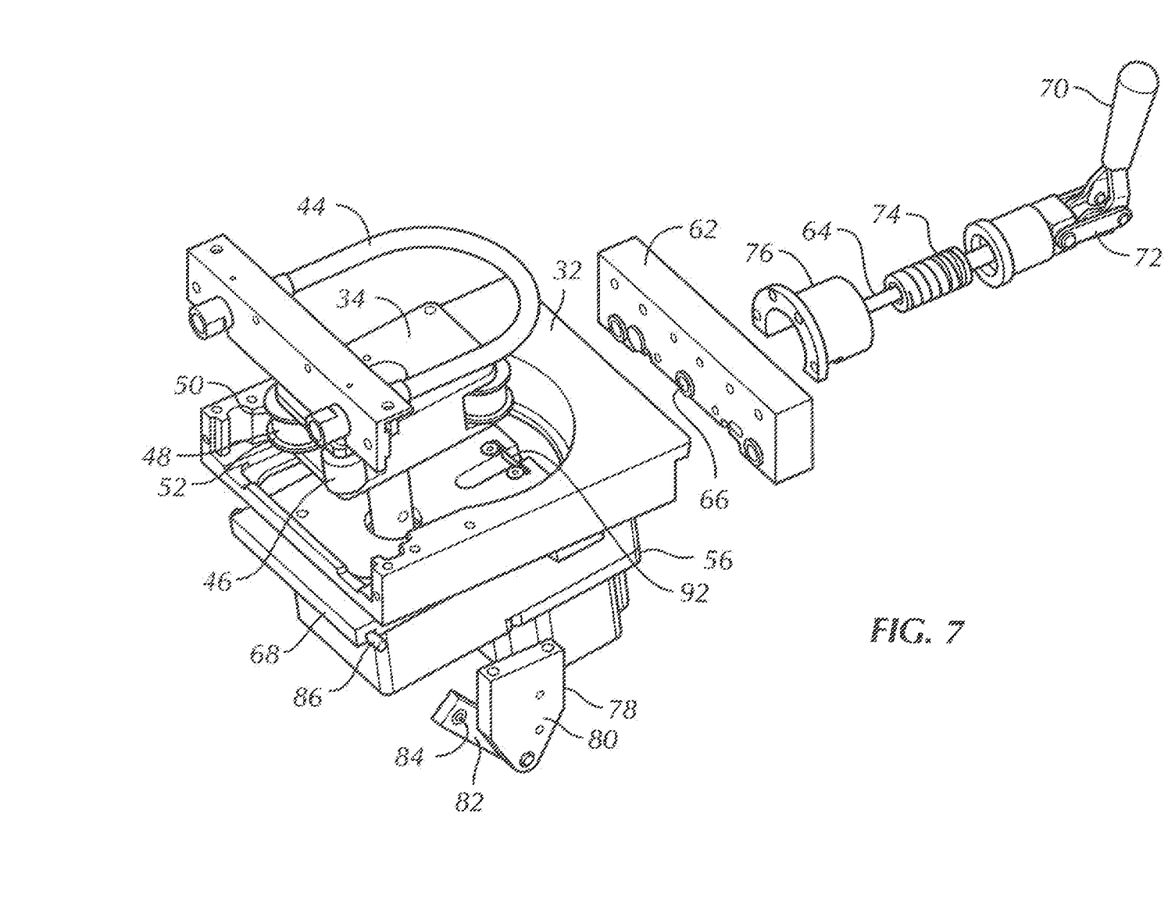

Also and focusing on FIG. 7, to support the motor mount 56 and attendant elements that move with it, two side brackets 78 may be provided on respective sides of the raceway 32 (only one bracket 78 shown in FIG. 7). A vertical flange 80 of the side bracket 78 may be affixed to the raceway 32, e.g., by threaded fasteners or welding, and a swing arm 82 pivotably coupled to the vertical flange 80 and rotatably coupled to the motor mount 56 or other component that moves with the motor mount 56. In the example shown in FIG. 7, a hole 84 is formed in the swing arm 82 and rotatably engages a pin 86 that is attached to and that extends radially away from the motor plate 68. Recall that, the motor mount 56, motor plate 68, and rotor 34 move translationally together as unit.

Figure 8:
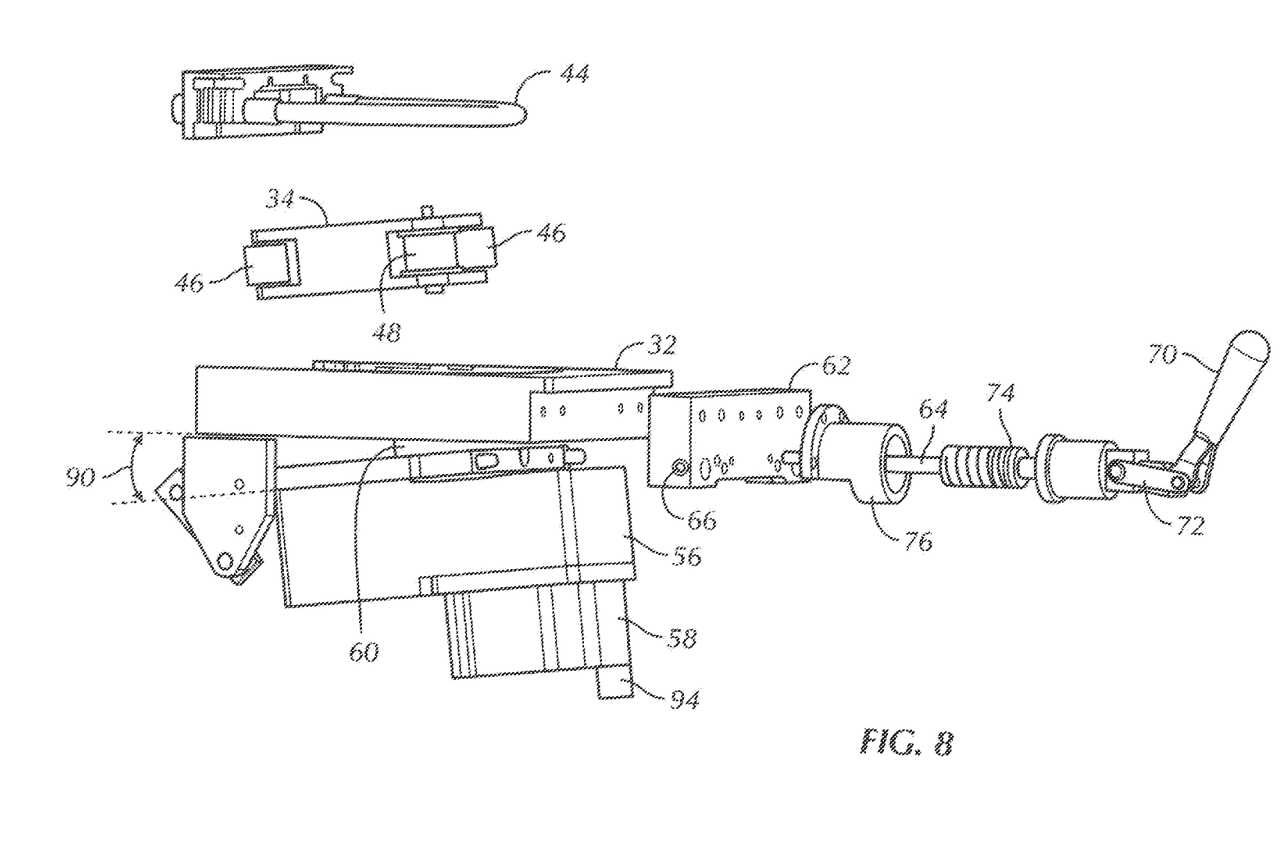
FIGS. 8 and 9 are exploded side views respectively showing the relationship between the motor mount and the raceway in the tube load and pump positions of the rotor, with some portions broken away.
Figure 9:
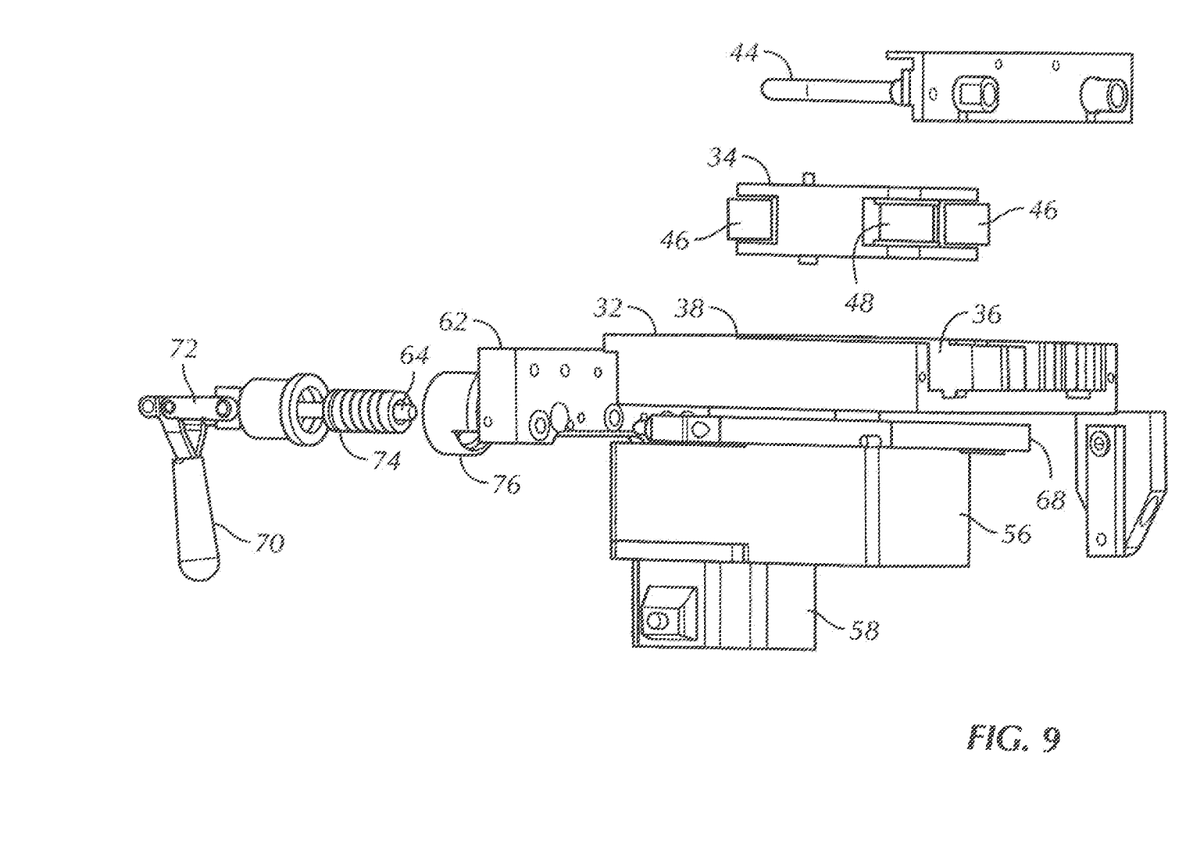

Owing to the example positioning mechanism described above, as best shown in FIG. 9 the motor mount 56 (with motor plate 68) is parallel to fee raceway 32 when the rotor 34 is m the pump position. In contrast, as best shown in FIG. 8, the motor mount 56 (with, motor plate 68) is obliquely angled relative to the raceway 32 when the rotor 34 is in the tube load position. That is, an oblique angle 90 is established between, for example, the plane of the motor plate 68 and the plane defined by the bottom surface of the raceway 32 when the rotor 34 is in the tube load position. To further facilitate motion of the positioning mechanism when the handle 70 is moved, a hinge pin 92 (FIG. 7) may be provided as part of the coupling between the push rod 64 and motor mount 56/motor plate 68.

Thus, the rotor 34 can move linearly relative to raceway 32. In the example shown, linear bearings are used, it being understood that equivalently a multi-bar linkage between the rotor 34 and raceway 32 can be used for pseudo-linear motion. In any case, in the tube position the rotor 34 is a sufficient distance (typically an inch or more) so that the tube 44 can be inserted freely between the rotor 34 and raceway 32 by a person. Then, when the rotor is moved to the pump position, at least the drive rollers 46 urge into the tube 44 sufficiently to stretch the tube 44 by an elongation of at least 3% and typically 3-15%. This elongation advantageously ensures that slack does not build up in the tubing as it wears and stretches during use. As understood herein, such slack can lead to kinking of the tubing or excessive wear.

FIG. 8 is used to schematically show that at least one angular position sensor 94 can be provided on the motor 58. Without limitation, the angular position sensor may be a Hall effect sensor, or a dc stepper motor revolution counter, or a potentiometer type sensor. The sensor 94 generates an output representative of the angular position of the motor. The sensor 94 may be coupled to the motor shaft or the output shaft 60 or other part of the rotating mechanism in the pump.

In any ease, the processor 20 shown in FIG. 1 can control the motor 58 and can receive the signal from the sensor 94. Using the signal from fee sensor 94, the processor 20 can prevent the motor 58 from stopping at an angular position corresponding to at least one roller 46/48 being in a predetermined angular location relative to the raceway 32. In an example, the predetermined location of the roller corresponding to the angular position at which the motor is prevented from stopping is at an arc end 40 or 42 of the raceway 32. This ensures that, particularly when a raceway arc of >180 degrees is used, the rollers will not be in the 12 o'clock and 6 o'clock positions (i.e., adjacent to the ends of the arc), which would interfere with the raceway even when the rotor is in the tube load position and thereby complicate tube loading and unloading.

Thus, the position sensor 94 can be coupled to the motor shaft to indicate critical, angular positions to avoid stopping the motor at these positions. The processor 20 can control the motor so that it will not stop on these critical positions. Alternately, the signal from the one or more sensors 94 can be used to indicate non-critical positions, with the processor 20 controlling the motor so it will always stop on these non-critical angular positions. Yet again, a mechanical means, mechanism or other element, e.g., a pin, may be used to ensure that the motor/rotor does not stop in critical positions.

Completing the description, the tube 44 may be configured as a loop as best shown in FIG. 6, with the ends of the loop engaged with a manifold 100 in fluid communication with the interior of the manifold 10, In turn, the interior of the manifold 100 may communicate with a cassette 102 such as the cassette shown and described in U.S. patent application Ser. No. 14/180,655, filed Feb. 24, 2014 and incorporated herein by reference. Such a cassette can be engaged with structure in the control system 14 to exchange heat with working fluid flowing through the cassette 102 and tube 44 and being circulated by the pump 30 shown and described herein to and from a heat exchange member such as the catheter 12 and/or pad 18.

Figure 10:
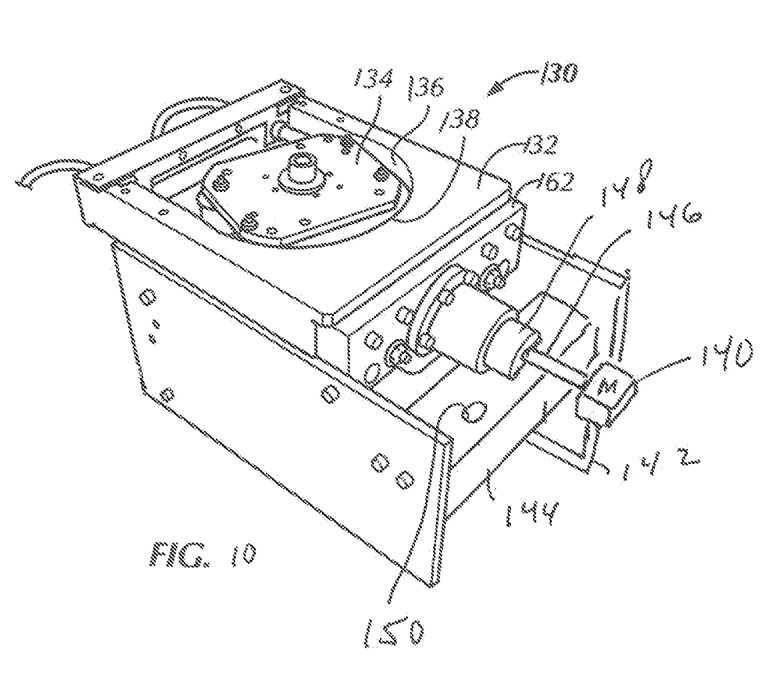
FIG. 10 is a perspective view of an alternate embodiment using a motor instead of a manually-operated handle with the rotor in the pump position, schematically illustrating the motor, gear, and operating button.

FIG. 10 shows an alternate embodiment 130 of the peristaltic pump that in all essential respects is identical in configuration and operation to the pump 30 described above with the exceptions noted. Like the pomp 30, the pump 130 in FIG. 10 includes a rigid, preferably metal or hard plastic raceway 132 and a rotor 134. The raceway 132 or channel may be formed from one or more blocks of material as shown, and has an inner arcuate surface 136 which may have a substantially constant radius of curvature. The arcuate surface 136 of FIG. 10 is substantially identical in configuration and operation to the arcuate surface 32 in FIG. 2. A motor rotates the rotor 134 relative to the raceway 132. As well, like the rotor 32 shown in FIG. 2, the rotor 134 shown in FIG. 10 may be movable translationally and/or rotationally relative to the raceway 132 between a pump position, in which the rotor 134 is spaced from the midpoint 138 of the inner surface 136 of the raceway 132 a first distance, and a tube load position in which the rotor 134 is spaced from the midpoint 138 a greater, second distance.

However, unlike the pump 30 shown is FIG. 2, the pump 130 shown in FIG. 10 provides a loading motor 140 to provide for automated or automatic movement of the rotor relative to the raceway, e.g., translational or rotational, instead of a manually-manipulable handle. Thus, the pump 130 in FIG. 10 omits, e.g., the handle 70 with hinge mechanism 72.

Instead, the loading motor 140, which may be mounted (e.g., directly on or by means of a bracket 142) to a pump base 144, reciprocatingly drives a push rod 146 to move the rotor 134 between the pump position and tube load position. Advantages associated with using a loading motor to move the rotor include but are not limited to the following: providing convenience tor the customer, e.g., the customer may not have to reach back and apply force to move the motor; the customer may not have access to moving parts; minimal or no room for the customer's hand may be needed, which in turn saves space; movement of the rotor may be controlled or allowed only when certain other conditions are met; the rotor may be moved with constant speed; and the force needed to move the rotor may be monitored. The motor 140 may be a direct current (dc) stepper motor or other ac or dc motor, or other appropriate motor type and the push rod 146 may be the rack element of a rack-and-pinion gear, with the pinion portion being geared to a shaft rotated by the motor 140. The push rod 146 may extend through a support block 162 that is substantially identical in configuration and operation to the support block 62 shown in FIG. 6 to contact and/or be engaged with a motor mount that supports the motor that rotates the rotor 134. One or more radial hearings 148 may be provided as appropriate to radially support elements of the positioning mechanism.

An operating button or key 150 may be manipulate by a person or controller to energize the loading motor 140. The button or key 150 may be positioned on the pump 130 base as shown and may be electrically connected to the controller of the motor 140, with the motor and its controller enclosed m the rectangular box shown at 140. In all other essential respects the pump 130 shown is FIG. 10 may be substantially identical in configuration and operation to the pump 30 shown in FIGS. 2-9.

Components included in one embodiment can be used in other embodiments in any appropriate combination. For example, any of the various components described herein and/or depicted in the Figures may be combined, interchanged or excluded from other embodiments.

"A system having at least one of A, B, and C" (likewise "a system having at least one of A, B, or C" and "a system having at least one of A, B, C") includes systems that have A alone, B alone, C alone, A and B together, A and C together, B and C together, and/or A, B, and C together, etc.

While various embodiments of HEAT EXCHANGE SYSTEMS FOR PATIENT TEMPERATURE CONTROL WITH EASY LOADING HIGH PERFORMANCE PERISTALTIC PUMPS are herein shown and described in detail, the scope of the present invention is to be limited by nothing other than the appended claims.

What is claimed is:

1. A pump, comprising:
   a raceway having an inner surface;
   a rotor body facing the inner surface of the raceway, the rotor body being rotatable relative to the raceway, the rotor body being mounted relative to the raceway between a pump position, wherein the rotor body is spaced from the inner surface of the raceway a first distance, and a tube load position, wherein the rotor body is spaced from the inner surface of the raceway a second distance greater than the first distance;
   an electric rotor motor coupled to the rotor body to rotate the rotor body,
   one or more rollers arranged on the rotor body to contact tubing disposed between the rotor body and the raceway at least when the rotor body is in the pump position; and
   an electric loading motor coupled to a motor mount supporting the electric rotor motor, the electric loading motor configured to move the motor mount at least rotationally, or both translationally and rotationally relative to the raceway to cause the rotor body to move between the pump position and the tube load position, wherein the electric loading motor reciprocatingly drives a push rod extending through a block and engaging a support of the rotor body to move the rotor body between the pump position and tube load position.

2. The pump of claim 1, wherein the inner surface of the raceway extends through an arc of at least one hundred eighty degrees (180°).

3. The pump of claim 1, wherein the one or more rollers comprise:
   at least one drive roller on the rotor body, the drive roller having a cylindrical outer surface, at least a portion of the outer surface being configured to urge against the tubing disposed between the rotor body and the raceway when the rotor body is in the pump position and is rotated, the drive roller having no flanges with peripheries extending beyond the cylindrical outer surface; and
   at least one guide roller on the rotor body, the guide roller having a cylindrical outer surface and top and bottom flanges defining respective peripheries extending beyond the cylindrical outer surface of the guide roller such that the tubing that is disposed between the rotor body and the raceway is received on the cylindrical outer surface of the guide roller between the flanges when the rotor body is in the pump position and is rotated.

4. The pump of claim 3, comprising a plurality of drive rollers and a plurality of guide rollers.

5. The pump of claim 3, comprising two and only two drive rollers and two and only two guide rollers.

6. The pump of claim 1, wherein the pump comprises an operating element manipulable by a person or a controller to energize the loading motor.

7. The pump of claim 1, wherein the raceway defines an arc and the arc defines opposed arc ends, and a predetermined location of a respective roller corresponding to an angular position at which the rotor motor is prevented from stopping is at an arc end.

8. The pump of claim 1, comprising:
   a controller configured for controlling the electric rotor motor; and
   an angular position sensor configured for sensing angular position of the electric rotor motor and generating a signal indicative thereof to the controller,
   wherein the controller is configured to:
      prevent the electric rotor motor from stopping at an angular position in which at least one roller is in a predetermined location of one or more predetermined angular positions corresponding to arc ends of the raceway or one or more non-critical positions of the rotor body corresponding to arc ends of the raceway.

9. The pump of claim 1, further comprising:
a controller configured to automatically prevent the rotor body from stopping at one or more predetermined angular positions or to control the electric rotor motor so it will stop on non-critical angular positions.

10. A method comprising:
rotating a peristaltic pump rotor body relative to a raceway to urge fluid through a tube disposed between the raceway and the rotor body; and
energizing a loading motor to move the rotor body away from the raceway, wherein the loading motor reciprocatingly drives a push rod coupled to a motor mount supporting the rotor body, the loading motor configured to move the motor mount either rotationally or both rotationally and translationally away from the raceway to move the rotor body between a pump position and a tube load position of the peristaltic pump rotor body.

11. The method of claim 10, comprising:
automatically preventing, by a controller, the rotor body from stopping at one or more predetermined angular positions so it will always stop on non-critical angular positions.

12. A pump assembly comprising:
a raceway that includes an arc having a first arc end and a second arc end;
a rotor body spaced from the raceway;
an electric rotor motor configured to rotate the rotor body to urge fluid through a tube disposed between the raceway and the rotor body;
a loading motor coupled to a motor mount supporting the electric rotor motor, the loading motor configured to move the motor mount either rotationally, or translationally and rotationally relative to the raceway to cause the rotor body to move between a pump position and a tube load position;
a button or key operable by a person or controller to energize the loading motor; and
a controller configured to:
automatically prevent the rotor body from stopping at one or more predetermined angular positions or to control the electric rotor motor so it will stop on non-critical angular positions, the one or more predetermined angular positions including the first arc end, the second arc end, or both the first arc end and the second arc end.

13. The pump assembly of claim 12, wherein the raceway has an inner surface extending through an arc of at least one hundred eighty degrees (180°), the arc defining a midpoint, and the rotor body faces the inner surface of the raceway.

14. The pump assembly of claim 12, wherein, for the pump position, the rotor body is spaced from the raceway a first distance, and
wherein, for the tube load position, the rotor body is spaced from the raceway a second distance greater than the first distance.

15. The pump assembly of claim 12, wherein the raceway extends through an arc of at least one hundred eighty degrees (180°).

16. The pump assembly of claim 12, comprising:
at least one drive roller on the rotor body, the drive roller having a cylindrical outer surface, at least a portion of the outer surface being configured to urge against the tube disposed between the rotor body and the raceway, the drive roller having no flanges with peripheries extending beyond the cylindrical outer surface; and
at least one guide roller on the rotor body, the guide roller having a cylindrical outer surface and top and bottom flanges defining respective peripheries extending beyond the cylindrical outer surface of the guide roller such that the tube disposed between the rotor body and the raceway is receivable on the cylindrical outer surface of the guide roller between the flanges.

17. The pump assembly of claim 12, comprising plural drive rollers and plural guide rollers on the rotor body.

18. The pump assembly of claim 12, comprising two and only two drive rollers and two and only two guide rollers on the rotor body.

19. The pump assembly of claim 12, wherein the raceway extends through an arc of at least two hundred degrees (200°).

20. The pump assembly of claim 12, wherein the rotor body is rectangular.

* * * * *

UNITED STATES PATENT AND TRADEMARK OFFICE
CERTIFICATE OF CORRECTION

PATENT NO. : 11,359,620 B2
APPLICATION NO. : 14/676682
DATED : June 14, 2022
INVENTOR(S) : Pamichev et al.

It is certified that error appears in the above-identified patent and that said Letters Patent is hereby corrected as shown below:

On the Title Page

Column 2, Line 2 item (56), (Other publications) delete "Clark" and insert --Clark,--

Column 2, Line 1 item (57), (Abstract) delete "wife" and insert --with--

Column 2, Line 3 item (57), (Abstract) delete "are" and insert --arc--

Column 2, Line 5 item (57), (Abstract) delete "transitionally" and insert --translationally--

Page 4, Column 2, Line 39 item (56), (Other publications) delete "Dasrowiak," and insert --Dabrowiak,--

Page 4, Column 2, Line 44 item (56), (Other publications) delete "Dasrowiak," and insert --Dabrowiak,--

Page 4, Column 2, Line 72 item (56), (Other publications) delete "14/676,504," and insert --14/675,504,--

In the Specification

Column 1, Line 20 delete "brain," and insert --brain--

Column 1, Line 41 delete "external," and insert --external--

Column 2, Line 5 delete "sway" and insert --away--

Column 2, Line 17 delete "wherein," and insert --wherein--

Column 2, Line 22 delete "contact," and insert --contact--

Signed and Sealed this
Fourth Day of April, 2023

Katherine Kelly Vidal
*Director of the United States Patent and Trademark Office*